(12) United States Patent
Borden et al.

(10) Patent No.: US 9,495,709 B2
(45) Date of Patent: Nov. 15, 2016

(54) INSURANCE PROCESSING SYSTEMS AND METHODS USING MOBILE DEVICES FOR PROOF OF INSURANCE

(75) Inventors: Richard M. Borden, West Hartford, CT (US); Andrew J. Amigo, Gloucester, MA (US); Keven J. Busque, Manchester, CT (US); David F. Peak, Avon, CT (US); Eugene J. Walters, Avon, CT (US)

(73) Assignee: HARTFORD FIRE INSURANCE COMPANY, Hartford, CT (US)

( * ) Notice: Subject to any disclaimer, the term of this patent is extended or adjusted under 35 U.S.C. 154(b) by 396 days.

(21) Appl. No.: 12/906,737

(22) Filed: Oct. 18, 2010

(65) Prior Publication Data

US 2011/0161118 A1    Jun. 30, 2011

Related U.S. Application Data

(63) Continuation-in-part of application No. 12/754,189, filed on Apr. 5, 2010, and a continuation-in-part of application No. 12/877,784, filed on Sep. 8, 2010.

(60) Provisional application No. 61/291,501, filed on Dec. 31, 2009.

(51) Int. Cl.
| | | |
|---|---|---|
| *G06Q 40/00* | (2012.01) |
| *G06Q 40/08* | (2012.01) |
| *G06Q 10/06* | (2012.01) |
| *G06Q 10/10* | (2012.01) |
| *G06Q 50/22* | (2012.01) |
| *G06F 19/00* | (2011.01) |
| *G06Q 50/24* | (2012.01) |

(52) U.S. Cl.
CPC ............ *G06Q 40/08* (2013.01); *G06F 19/323* (2013.01); *G06F 19/3418* (2013.01); *G06F 19/366* (2013.01); *G06Q 10/067* (2013.01); *G06Q 10/10* (2013.01); *G06Q 50/22* (2013.01); *G06Q 50/24* (2013.01)

(58) Field of Classification Search
CPC .............................. G06Q 40/00; G06Q 40/08
USPC ............................................................ 705/4
See application file for complete search history.

(56) References Cited

U.S. PATENT DOCUMENTS

| | | | | |
|---|---|---|---|---|
| 6,313,791 | B1 * | 11/2001 | Klanke ................... 342/357.75 |
| 8,140,358 | B1 * | 3/2012 | Ling et al. ....................... 705/4 |
| 2003/0069761 | A1 * | 4/2003 | Nozaki et al. .................... 705/4 |
| 2010/0174564 | A1 | 7/2010 | Stender et al. |
| 2010/0280748 | A1 * | 11/2010 | Mundinger et al. ........... 701/200 |

* cited by examiner

*Primary Examiner* — Eric T Wong
(74) *Attorney, Agent, or Firm* — Howard IP Law Group, PC

(57) ABSTRACT

Systems, methods, apparatus, means and computer program code for operating a mobile device and an insurance processing system are provide which include receiving, from a mobile device, sensor data collected from at least a first sensor of the mobile device, determining, based at least in part on the sensor data, that an activity associated with an insured is not covered by a plurality of insurance coverage rules, and transmitting, to the mobile device, information indicating that an activity is not covered by a plurality of insurance coverage rules.

15 Claims, 14 Drawing Sheets

INSURANCE PROCESSING SYSTEMS AND METHODS USING MOBILE DEVICES FOR PROOF OF INSURANCE

CROSS REFERENCE TO RELATED APPLICATIONS

The present application is based on, and claims benefit and priority of, U.S. Provisional Patent Application Ser. No. 61/291,501 filed on Dec. 31, 2009, and U.S. patent application Ser. Nos. 12/754,189, and 12/877,784 filed on Apr. 5, 2010, and Sep. 8, 2010 respectively, the contents of each of which are incorporated herein in their entirety for all purposes.

FIELD

Embodiments relate to insurance processing systems and methods. More particularly, embodiments relate to the use of mobile devices to provide proof of insurance as well as to obtain additional coverage.

BACKGROUND

Many types of insurance policies provide coverage that is, at least in part, based on location or type of activity. For example, automobile policies provide coverage in a geographical area (e.g., such as within the United States). Commercial line insurance policies for contractors often provide coverage for a specific job site or location and for specific types of activities (e.g., a carpenter may specifically be covered for performing finishing work on a residential site, but may not be covered for roofing a home). Many types of service providers or contractors, such as commercial builders, carry small commercial line insurance policies which require that each job site the contractor works on be added as a rider to the small commercial policy. This ensures that the job site and the contractor's work (including their employees) are properly covered by the policy. Oftentimes, contractors forget to obtain these riders or fail to obtain them prior to starting a project. It would be desirable to make it easier for insureds to verify or obtain proof of coverage and, if necessary, to easily obtain any additional coverage needed.

Other types of insurance, such as personal lines policies, require riders or additional coverage for certain types of activities. For example, some personal lines policies require additional coverage for individuals who participate in certain risky activities (such as piloting a small aircraft). Many individuals fail to obtain this additional coverage as the process is not convenient. As another example, many automobile policies do not cover U.S. licensed drivers when they are in Mexico or Canada (or other countries), and require a rider to cover driving outside the U.S. Again, many drivers do not obtain such additional coverage, as the process is not convenient. It would be desirable to allow such coverage to be applied for and issued using a mobile device.

Frequently, events or circumstances or may occur for which a person or entity should have insurance coverage for, but they do not either through lack of awareness or an inability to easily obtain appropriate coverage. For example, homeowners or businesses that live in an area that is in the path of a forest fire or likely will be in the range of a fire during a particularly dry period may not be aware of their insurance options. It would be desirable to inform such individuals or businesses of their options and allow the issuance and binding of coverage using mobile devices.

Further, it would be desirable to provide proof of insurance as needed. For example, a building inspector visiting a job site may request that a contractor provide proof of insurance. It would be desirable to provide mobile device systems and methods which allow for ready proof of insurance to be provided.

DETAILED DESCRIPTION

Embodiments of the present invention relate to systems and methods for proving or verifying insurance coverage. Further, some embodiments provide systems and methods for obtaining additional insurance coverage on an as-needed basis. In some embodiments, requests for additional insurance coverage may be initiated by proactive requests from an insured (e.g., where a contractor knows he needs additional coverage for a new job site), while in other embodiments, requests for additional insurance coverage may be triggered based on information received by an insurance company from a mobile application associated with an insured (e.g., where a driver may not know she needs additional insurance coverage outside the U.S., and is driving through a border crossing into Mexico).

In some embodiments, mobile devices, such as smart phones, tablet computers, or other portable communication and computing devices, are provided with software (referred to herein as "applications," "mobile applications," or "mobile insurance applications") that allow users to easily verify or prove the extent of insurance coverage of an individual or entity. Some embodiments allow users to obtain additional insurance coverage on an as-needed basis by interacting with an insurance company through a mobile insurance application. In this manner, embodiments allow insured individuals or entities to easily prove or verify insurance coverage and to obtain any needed additional coverage when and where they need it. Requests for additional coverage may be proactively requested by insureds, or triggered based on usage, location or other activity data received by an insurance company from a mobile application operated on a mobile device carried by an insured.

Figure 1:
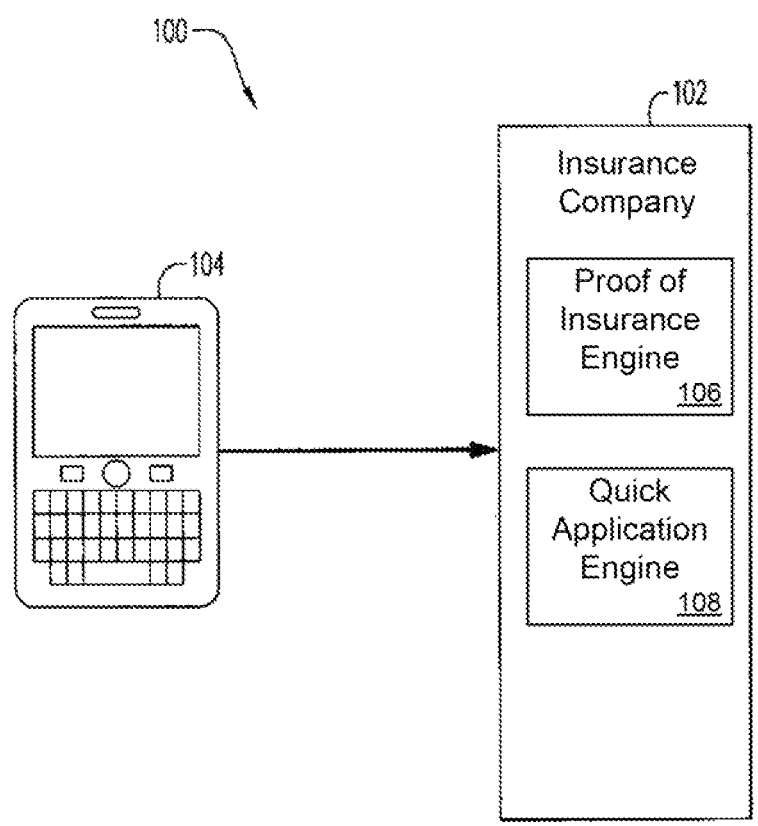
FIG. 1 illustrates a system architecture within which some embodiments may be implemented.

Features of some embodiments will now be described by reference to FIG. 1, which is a block diagram of an insurance processing system 100 pursuant to some embodiments. As shown in FIG. 1, a system 100 includes a mobile device 104 in communication with an insurance company 102. The mobile device 104 may be a device operated by an individual insured by the insurance company 102 or a device operated by an individual attempting to verify the status of insurance coverage of an insured individual. Examples of various embodiments are illustrated below in FIG. 7A (in the case of an individual attempting to verify the status of insurance coverage of an insured), in FIG. 7B-C (in the case of an insured checking the status of their coverage and obtaining added coverage), and in FIG. 9 (in the case of an insured being notified by an insurance company that their usage, location, and/or activity suggests that additional insurance coverage may be required).

The insurance company 102 operates systems to store information associated with existing policies, and operates computer program code allowing the verification or proof of insurance coverage (shown as proof of insurance engine 106). The insurance company 102 further may operate computer program code allowing insured individuals to obtain additional or updated coverage by submitting requests via a mobile device 104 (shown as a quick application engine 108). In some embodiments, the quick application engine 108 operates to analyze usage data from mobile device 104 to identify usage patterns, locations, or activity data which may indicate that an insured requires additional insurance coverage. While such embodiments will be described further below in conjunction with FIGS. 8 and 9, in general, an insured may consent to provide usage, location and/or activity data (collected in a mobile insurance application) to insurance company 102 on a regular basis. Insurance company 102 analyzes the data to detect patterns which may indicate that the insured requires additional insurance coverage. For example, a driver who has an automobile policy may operate a mobile device 104 which has a mobile insurance application that transmits location data to insurance company 102. If the location data indicates that the driver is, or will be, passing outside a geographical area in which the driver is covered, the insurance company 102 may send a notification to the driver asking them to confirm whether additional coverage is desired (and, in some embodiments, reminding the driver of the limits of their existing coverage). Embodiments may be used in conjunction with a variety of different insurance policy types, including with personal lines policies, commercial policies, life insurance policies, heath insurance policies, workers compensation policies or the like.

In some embodiments, the quick application engine 108 and/or the proof of insurance engine 106 may be operated or maintained by entities other than the actual insurer, such as, for example, an agent of the insurance company 102 or other service provider. For ease of exposition, however, the systems and processes herein will be described as being performed by an insurance company 102.

Pursuant to some embodiments, a mobile insurance application may be stored in, or accessible to, a memory of mobile device 104 which allows a user of the mobile device to obtain proof or verification of insurance coverage of an individual and/or to allow insured individuals to obtain additional coverage (e.g., for a specific project, task or activity). The terms "individual" or "insured individual" are used herein for convenience and ease of exposition, and are intended to refer to individual policy holders as well as actors or agents of an insured individual (e.g., in the case of commercial lines policies covering or involving the actions of a number of employees, each employee may be referred to as an "individual" or "insured individual"). The term "user" is used herein to refer to an individual who carries or uses a mobile device 104 which has a mobile insurance application pursuant to the present invention installed thereon. A "user" may be an "insured individual".

Those skilled in the art, upon reading this disclosure, will appreciate that embodiments of the present invention may be used in conjunction with a number of different types of insurance coverage. For example, embodiments of the present invention allow mobile devices to be operated to provide proof of insurance as well as to obtain additional coverage for personal lines policies, commercial policies, life insurance policies, heath insurance policies, workers compensation policies or the like.

As an example, many types of contractors, such as commercial builders, carry small commercial insurance policies which require that each job site the contractor works on be added as a rider to the small commercial policy. This ensures that the job site and the contractor's work (including their employees) are properly covered by the policy. Oftentimes, contractors forget to obtain these riders or don't get them prior to starting. It would be desirable to make it easier for users to obtain quick coverage. Further, it would be desirable to provide proof of such insurance as needed. For example, a building inspector visiting a job site may request that the contractor provide proof of insurance. Embodiments of the present invention allow users of mobile devices 104 to quickly obtain short term policies (such as riders to existing policies) and to provide proof of such insurance.

Pursuant to some embodiments, a user of a mobile device 104 may launch an insurance application stored on the device 104 to obtain a short term policy or a rider. The application may prompt the user for details of the coverage requested, as well as details about the job site (or other details about the act or location to be covered). In some embodiments, the application may prompt the user to take one or more pictures or videos of the job site or location. The application data, pictures or video, and geocoded location data are transmitted to the insurance company 102 for underwriting and processing (e.g., using quick application engine 108). If the coverage is granted, a certificate showing proof of insurance is transmitted from the insurance company 102 to the user's mobile device 104 for use in proving the coverage as needed.

As another example, many drivers restrict their driving to a local area, driving to work, school and to perform local errands. Such drivers may select an insurance policy which only covers local or limited driving. Pursuant to some embodiments, when such an insured takes a longer trip, the present invention allows the generation of a notification to the insured that their trip may not be covered by their current policy, and presents the insured with proposed additional coverage sufficient to cover the trip. The additional coverage may be based on a route or trip plan identified by the insured, or it may be based on geolocation data received from a mobile device 104 associated with the insured. For example, an insured that operates a mobile device 104 having an insurance application of the present invention may receive automated notifications triggered by the insured's travel outside of the insured's covered area. The notifications may allow the insured to obtain additional coverage based on the insured's actual location and travel information.

As a still further example, homeowners, tenants and business owners operating mobile devices 104 with insurance applications pursuant to the present invention may receive notifications associated with their property or safety based on events that may present an insurance or safety risk to the insured. For example, a homeowner whose home is in the path of a wildfire may receive a notification of the details and location of the wildfire. Such a notification may include safety or property protection instructions and steps that can be taken by the insured to avoid injury and reduce the potential for property loss or damage, such as evacuation instructions, emergency information, or the like. Such a notification may also include information regarding the insured's coverage and whether any additional coverage may be obtained. In the event that additional coverage may be obtained, the insured may interact with the mobile device 104 to bind the additional coverage. Pursuant to some embodiments, the location of the mobile device 104 as well as the location of the insured's property may trigger such notifications. A user visiting Florida (as detected by a geolocation of their mobile device 104) during a hurricane may receive a hurricane warning, evacuation instructions and policy information. A user who has a home in Southern California that may be in the path of a wildfire may receive a fire warning, evacuation instructions and policy information based on the location of the home.

In some embodiments, mobile device 104 may further function as a payment device, allowing an insured user to receive or access funds relating to an insurance claim. For example, in a situation where an insured suffers a property loss, such as from a fire or other disaster, embodiments allow the insured to receive funds allowing the insured to obtain temporary lodging, shelter or obtain other short term needs. In some embodiments, the mobile insurance application of the mobile device includes an electronic wallet or other payment account or payment account access device allowing the funds to be delivered to, or associated with a payment account accessible to the insured by operating the mobile device 104. Other features, notifications, coverage verification and coverage binding applications will be described further below.

The mobile device 104 may be any of a number of different types of mobile devices that allow for wireless communication and that may be carried with or by a user. For example, in some embodiments, mobile device 104 is a smart phone such as an iPhone®, a mobile device operating the Android® operating system, or other portable computing device having an ability to communicate wirelessly with a remote entity such as insurance company 102).

Figure 5:
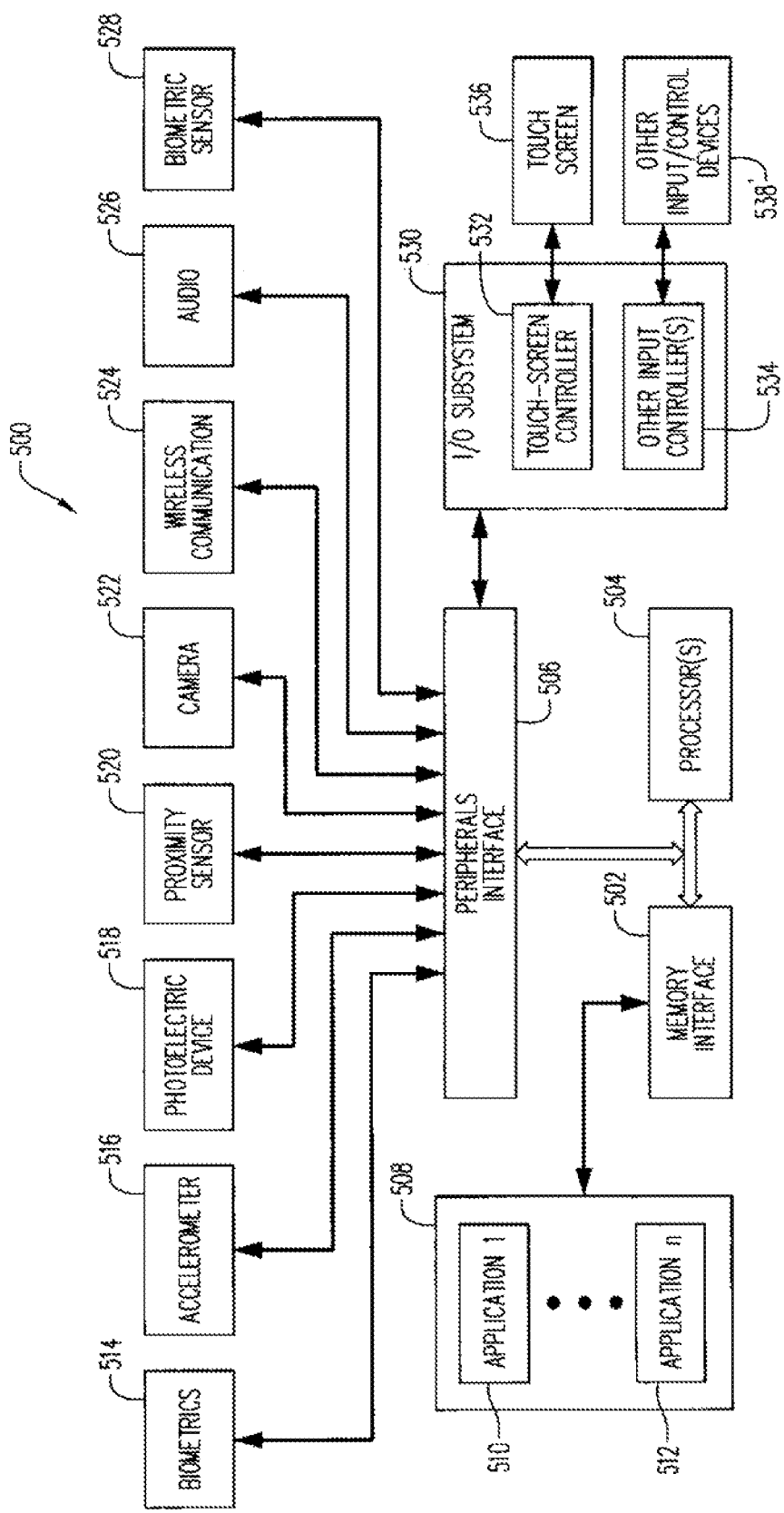
FIG. 5 is a partial functional block diagram of a mobile device and system provided in accordance with some embodiments.

Features of mobile devices 104 will be described further below in conjunction with FIGS. 5 and 6. Preferably, in some embodiments, mobile device 104 is capable of communicating with remote systems (such as insurance company 102) via wireless communication techniques (as will be described further below in conjunction with FIG. 2), and is further capable of receiving as well as capturing information associated with a potential activity for which insurance coverage is sought (e.g., such as photos or images of a contractor job site, etc.) or for which insurance coverage or information is desirable (e.g., such as location information, natural disaster or weather-related information, etc.). In some embodiments, the information may be captured using a camera or other image capture device, while in some embodiments, sensors (such as RFID sensors) may be used. In some embodiments, information identifying an activity for which coverage verification or new coverage is sought may include data that is key-entered by a user of the mobile device 104. Pursuant to some embodiments, information identifying an activity may be automatically captured by one or more sensors or components of the mobile device 104 and transmitted to an insurance company 102 or other entity for analysis and possible further action.

Pursuant to some embodiments, operation of the mobile device 104 for the verification of coverage as well as obtaining additional coverage is controlled by one or more mobile insurance applications stored in a memory of the mobile device 104.

In some embodiments, the mobile insurance application includes functionality to verify or authenticate the identity of the user so that the insurance company 102 can verify that the data was collected from the correct user. A number of different verification and authentication methods may be used in conjunction with embodiments of the present invention. For example, a user may be prompted to enter a secure password or personal identification number prior to receiving information about a potential activity for which coverage or verification of insurance is sought and transmitting the information to the insurance company 102. Alternatively or in addition, users may be identified and authenticated using location information, biometric information or other information captured using sensor(s) of the mobile device 104. The verification may be controlled by the mobile insurance application or it may require communication with a verification system associated with the insurance company 102. In some embodiments, once a user is successfully authenticated or verified, the mobile insurance application may prompt the user to capture specific information about a proposed activity for which insurance coverage or verification is sought (e.g., such as taking one or more photos of a job site or a vehicle, etc.) as well as entering additional meta data associated with the activity so that the information may be transmitted to the insurance company 102 and either processed using proof of insurance engine 106 or used to generate an application for additional coverage using the quick application engine 108.

Pursuant to some embodiments, data may be transmitted between devices using a wireless network. In some embodiments, some, or all, of the data may be transmitted using other network communication techniques (e.g., such as satellite communication, RFID, or the like). In some embodiments, some or all of the data transmitted between devices may be encrypted or otherwise secured to prevent intrusion.

Figure 2:
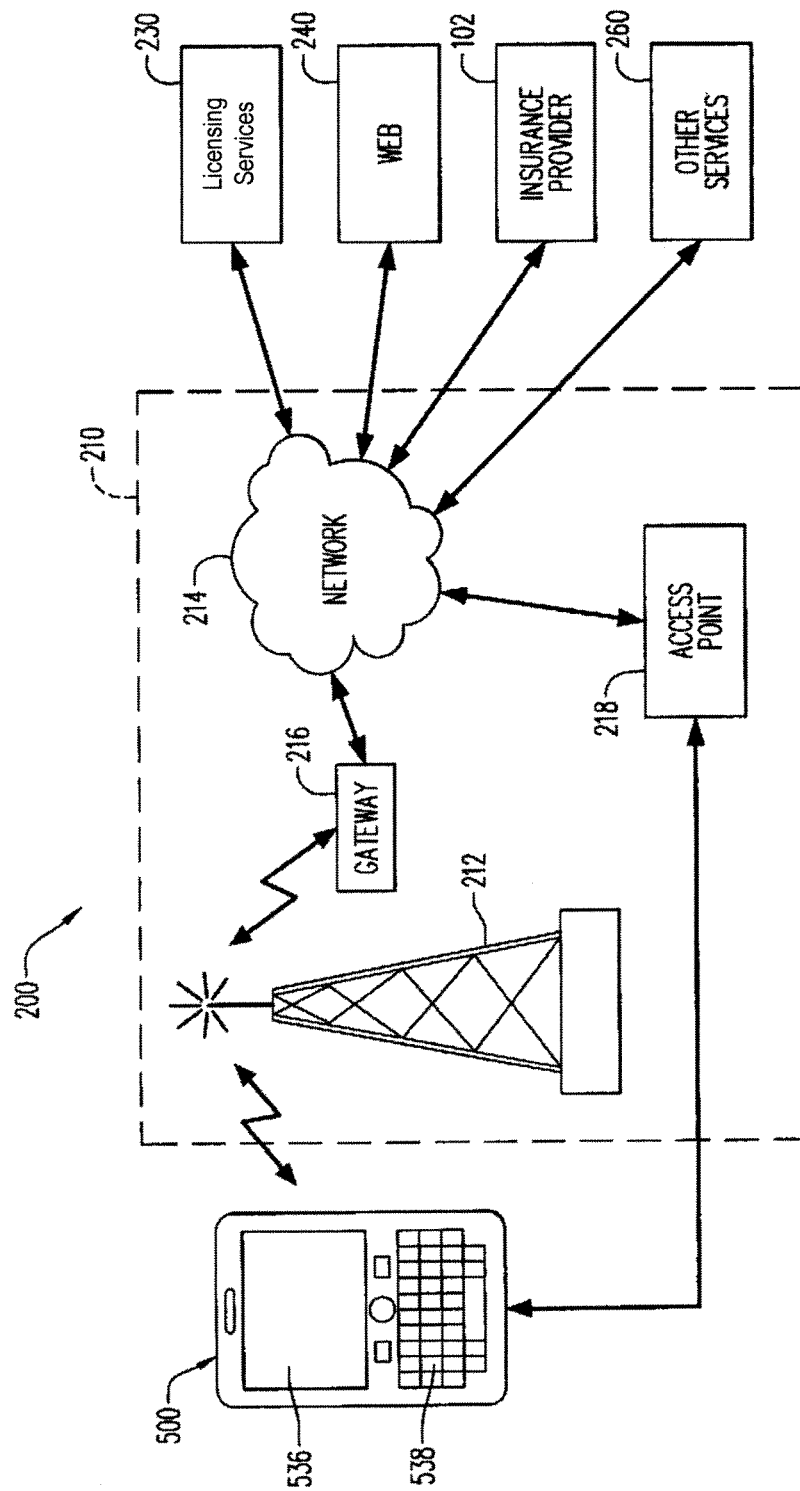
FIG. 2 illustrates a mobile system architecture within which some embodiments may be implemented.

Reference is now made to FIG. 2, which is a block diagram of an example network environment 200 showing communication paths between a mobile device 500 and the insurance provider systems 102 (as well as other devices and data sources). The mobile device 500 may be, for example, a mobile telephone, PDA, personal computer, or the like. For example, the mobile device 500 may be an iPhone® from Apple, Inc., a BlackBerry® from RIM, a mobile phone using the Google Android® operating system, a portable or tablet computer (such as the iPad® from Apple, Inc.), or the like. Pursuant to some embodiments, the mobile device 500 may be operated to capture data associated with one or more activities for which insurance coverage or verification of coverage is sought, append meta data to the captured data (such as geocode data, time stamp data, user-input data such as application data, activity descriptions, etc) and transmit the item data to an insurance provider 102 via a network 210. In general, mobile device 500 may be any mobile computing and/or communications device which is capable of executing the mobile insurance applications described herein.

The mobile device 500 of FIG. 2 can, for example, communicate over one or more wired and/or wireless networks 210. As an example, a wireless network can be a cellular network (represented by a cell transmitter 212). A mobile device 500 may communicate over a cellular or other wireless network and through a gateway 216 may then communicate with a network 214 (e.g., such as the Internet or other public or private network). An access point, such as access point 218 may be provided to facilitate data and other communication access to network 214. The access point 218 may be, for example, compliant with the 802.11g (or other) communication standards.

In some embodiments, mobile device 500 may engage in both voice and data communications over the wireless network 212 via access point 218. For example, the mobile device 500 may be able to place or receive phone calls, send and receive emails, send and receive short message service ("SMS") messages, send and receive email messages, access electronic documents, send and receive streaming media, or the like, over the wireless network through the access point 218. Similar communications may be made via the network 212.

In some embodiments, a mobile device 500 may also establish communication by other means, such as, for example, wired connections with networks, peer-to-peer communication with other devices (e.g., using Bluetooth networking or the like), etc.

The mobile device 500 can, for example, communicate with one or more services over the networks 210, such as service providers 230-260 and the insurance provider systems 102 (described above in conjunction with FIG. 1 and further below in conjunction with FIG. 3). For example, the mobile device 500 may communicate with one or more licensing services 230 to obtain verification or proof of licensing status of an individual or entity (e.g., in conjunction with the verification of insurance, in some embodiments, users of mobile devices 500 can request verification of a licensing status of an individual or entity by interacting with a mobile insurance application operating on mobile device 500). As another example, the mobile device 500 may communicate with one or more web services 240 to receive or transmit data to obtain licensing, status or other information. The mobile device may also be in communication with a number of other service providers 260.

For example, in embodiments where an insurance company system 102 provides payment or otherwise desires to advance funds to an insured, the mobile device 500 may be in communication with a payment network service provider operating to provide access to funds via the mobile device 500. In one illustrative embodiment, a payment network service provider may be a payment account issuing financial institution that receives funds from the insurance company system 102 and holds them in an account associated with the user operating mobile device 500. The account may be, for example, a prepaid account accessible via a payment network such as those operated by Visa Inc. or MasterCard International Incorporated.

The mobile device 500 can also access other data over the one or more wired and/or wireless networks 210. For example, content providers, such as news sites, RSS feeds, web sites, blogs, social networking sites, developer networks, etc., can be accessed by the mobile device 500. Such access can be provided by invocation of a web browsing function or application (e.g., a browser) in response to a user launching a Web browser application installed on the mobile device 500.

The mobile device 500 can perform a number of different device functions which can be controlled or specified by the insurance company by providing instructions, data or commands to the mobile device 500. The instructions, data or commands may be executed by a processor of the mobile device 500 causing the mobile device 500 to be, effectively, under control of the insurance company allowing the insurance company to control the collection of insurance request data received from a mobile device. For example, the mobile device may be caused to collect application information regarding a request for an insurance rider to obtain coverage of an otherwise uninsured activity. The mobile device 500 may also be caused to operate to collect information about an individual or entity so that a verification of insurance status may be provided.

The mobile device 500 may operate as a telephone, an email device, a network communication device, a media player device, etc., under control of one or more applications installed on the mobile device 500. In some embodiments, a user operating the mobile device 500 may interact with the applications using a keypad 538 which may be a tactile keypad with individual keys, or which may be a touch screen keypad. The user is presented with information and graphics on a display screen 536. For example, a user who is operating a mobile insurance application pursuant to the present invention may be presented with a series of user interfaces which may: (1) instruct the user how to enter or obtain information about an individual or entity for the verification of insurance status for that individual or entity, and/or (2) instruct the user how to complete a request for additional insurance coverage for an activity or event.

Figure 3:
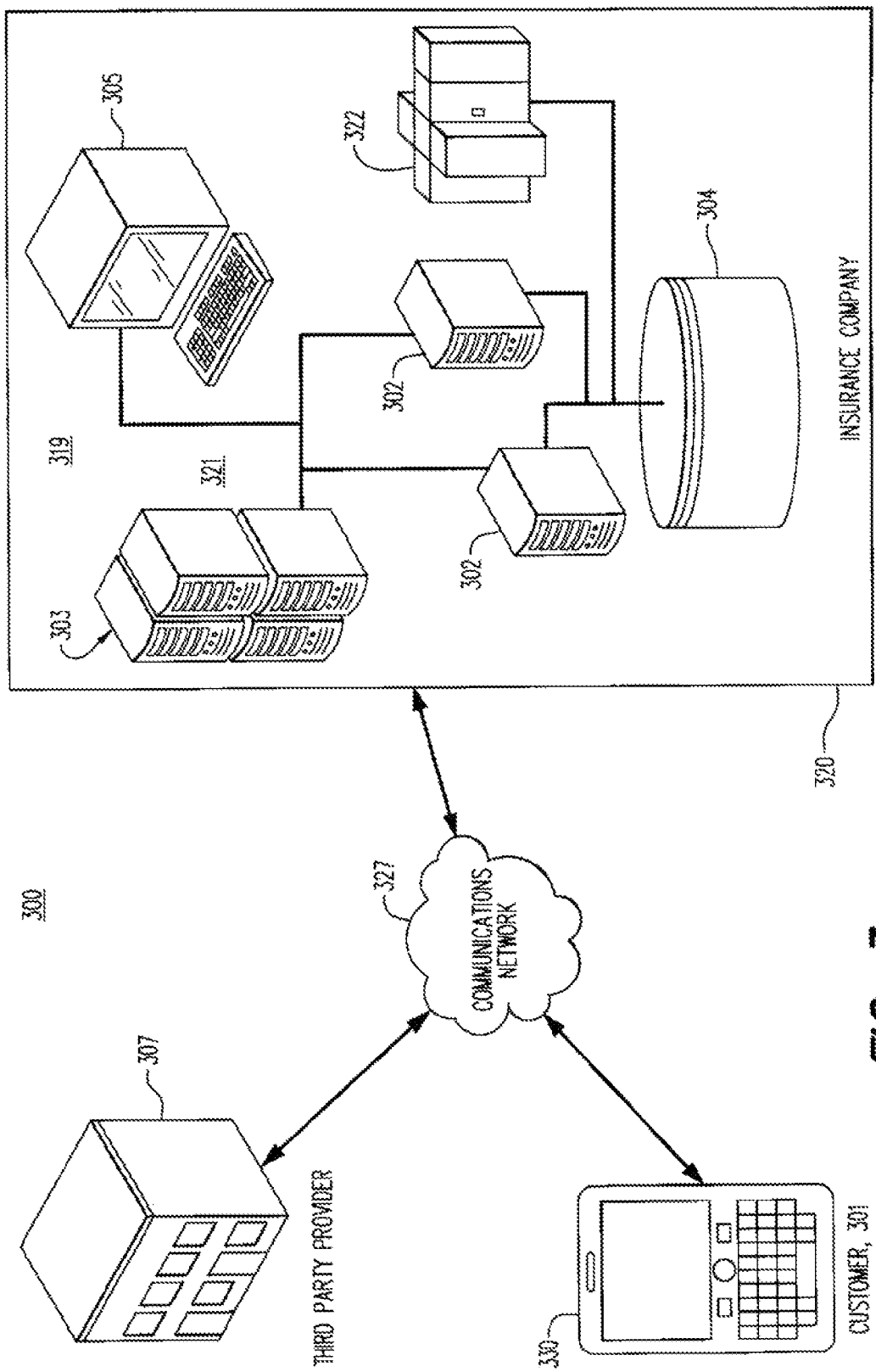
FIG. 3 is a block diagram of an insurance system pursuant to some embodiments.

Reference is now made to FIG. 3 which is a schematic diagram of a system 300 for providing proof of insurance coverage, analyzing coverage associated with insureds and activities, and for providing additional insurance coverage in the event that an event or activity is not covered by an existing policy. In FIG. 3, insurance company 320 provides customer 301 with insurance coverage. Insurance company 320 can simultaneously provide services to multiple customers, although only one customer 301 is shown in FIG. 3 for clarity.

Mobile device 330, pursuant to some embodiments, stores a mobile insurance application program that may be loaded onto the mobile device 330 from an insurance company 320 or from an application repository (e.g., such as Apple's App Store or the like). The application, when launched, prompts the customer 301 for information used to interact with the insurance company 320 or to collect and provide requests about insurance coverage to the insurance company 320. A variety of different types of data and information may be provided from mobile device 330 to insurance company 320, including static data regarding the customer 301, such as the customer's name, address, contact information, policy information, etc. Other variable information may be provided (as described in each of the mobile application embodiments described herein). Dynamic or collected data may also be provided by collecting data from one or more sensor(s) 332 in communication with the mobile device 330. In some situations, where appropriate permissions have been granted by the insured, data may be automatically collected by one or more sensor(s) 332 and transmitted to the insurance company 320 for processing. For example, some users may agree to provide location data to the insurance company 320 to qualify for or participate in "pay as you go" or metered automobile insurance policies, or to receive location-based weather or disaster related alerts or warnings.

Insurance company 320 has a computer system 319 that includes application servers 302, load balancing proxy servers 303, data storage unit 304, business logic computer 322, and user interface module 305 to perform risk evaluation and underwriting based on the collected location or activity data and policy information. Employees of the insurance company 320 and other authorized personnel use user interface module 305 to access the insurance company computer system. User interface module 305 may be any type of computing device that is configured to communicate with other computer systems. User interface module 305 may be connected directly to application server 302, or may access an application server 302 via the load balancing proxy servers 303. User interface module 305 may connect to load balancing proxy servers 303 via a local area network, a private data link, or via the internet.

Although depicted as being part of insurance company 320 in FIG. 3, user interface module 305 may be located remotely. The business logic computer 322 is connected to the data storage unit 304 and application servers 302 over a local area network 321, which may be part of communication system 327. In addition, other network infrastructure, including, for example a firewall, backup servers, and back up data stores, may also be included in the system 319, without departing from the scope of the invention. Communications over the local area network 321 and/or over the Internet, in one implementation, may be encrypted. In addition, such communications, whether encrypted or not, may also be digitally signed for authenticating the source of the communications. The computer system 319 may also include a certificate authority to authenticate one or more of the communications using public key infrastructure.

Based on property data collected from the mobile device 330 and any third party data sources, an evaluation module analyzes and evaluates data associated with a customer 301. As used herein, a "module" may be implemented in software for execution by various types of processors. An identified module of executable code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

As used herein, a module of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. In addition, entire modules, or portions thereof, may also be implemented in programmable hardware devices such as field programmable gate arrays, programmable array logic, programmable logic devices or the like or as hardwired integrated circuits.

A number of different business logic modules may be operated by insurance company 320 to process data collected by mobile devices 330. For example, a proof of insurance module or engine may be implemented, for example, in business logic computer 322, and used to respond to requests for proof of insurance coverage received from mobile devices 330. As another example, a quick application engine may be implemented, for example, in business logic computer 322 and used to generate and process applications for insurance riders or extensions of coverage received from mobile devices 330. Other modules may be provided to manage and administer functions including: payment account funding and payment decisioning, alerts and notifications, and the like. The business logic modules may use predictive models, such as neural networks, Bayesian networks, and support vector machines, in performing the underwriting and premium or coverage adjustment.

In one implementation, software operating on the application servers 302 act merely as presentation and data extraction and conversion servers. All substantive business logic, including underwriting and pricing determinations, is carried out on the business logic computer 322. In this implementation, the application servers 302 obtain data from the data storage unit 304 and the business logic computer 322 and incorporate that data into web pages (or other graphical user interface formats). These web pages are then communicated by the application servers 302 through the load balancing proxy servers 303 to user interface module 305 for presentation. Upon receiving input from user interface module 305, the application server 302 translates the input into a form suitable for processing by the business logic computer 322 and for storage by the data storage unit 304. In this implementation, the application servers can be operated by third parties, who can add their own branding to the web pages or add other customized presentation data. Alternatively or in addition, at least some of the business logic is also carried out by the application servers 302.

In some embodiments, the application servers 302 are software modules operating on one or more computers. One of the computers on which the application servers 302 are operating may also serve as the business logic computer 322 and/or as a load balancing proxy server 303.

In some embodiments, the software operating on user interface module 305 includes a thin or thick client application in addition to, or instead of a web browser. The thin or thick client application interfaces with a corresponding server application operating on the application server 302.

Figure 4:
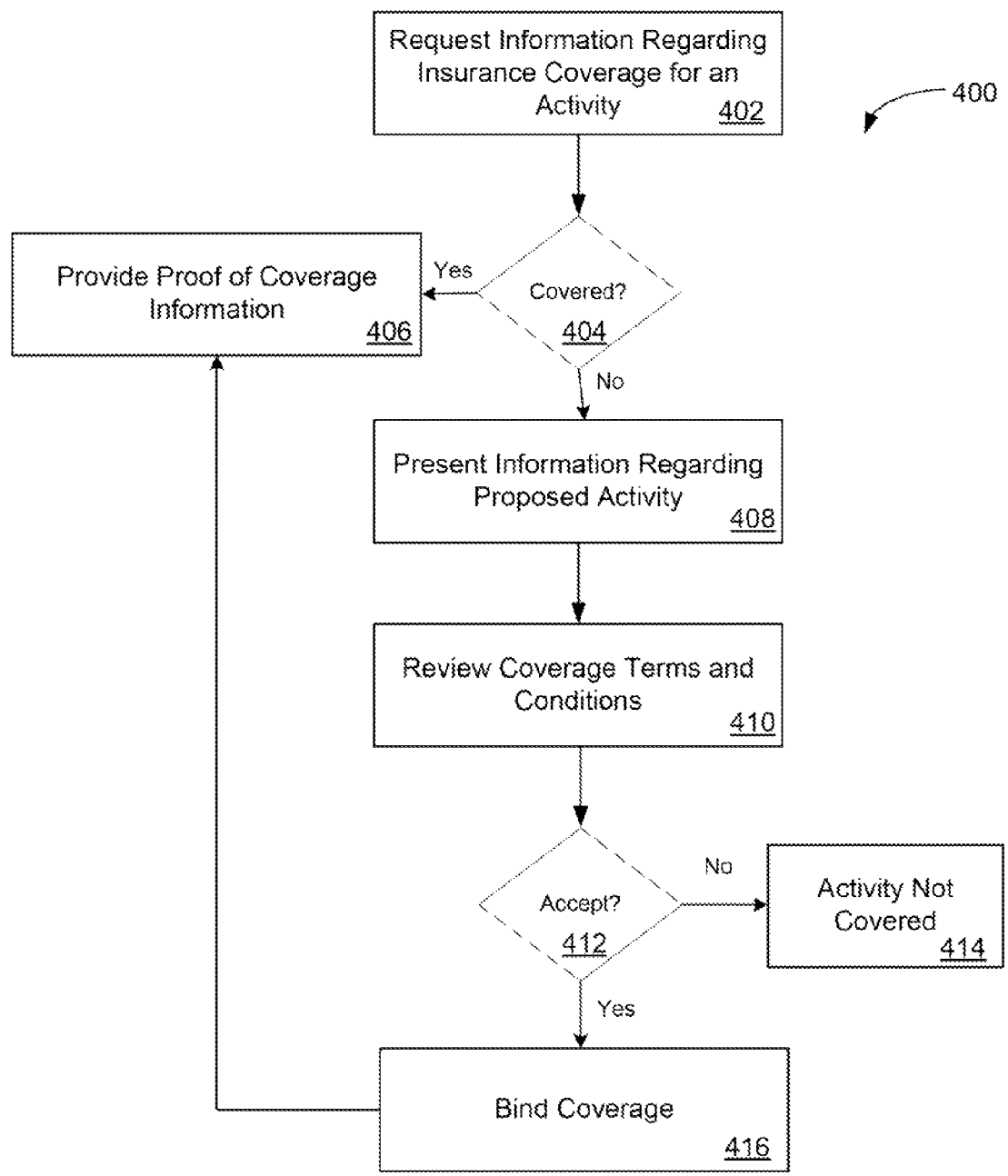
FIG. 4 is a flow diagram depicting a proof of insurance process pursuant to some embodiments.

Reference is now made to FIG. 4 which is a flow diagram depicting a process 400 for operating a mobile insurance application pursuant to some embodiments. Some or all of the steps of process 400 may be performed using a mobile device such as the mobile device 104 of FIG. 1 (or the mobile device 500 described in further detail below in conjunction with FIGS. 5 and 6). In the process 400, an operator of a mobile device 500 seeks to verify coverage for an activity under an insurance policy. In some embodiments, mobile devices may be operated by third parties to verify the insurance coverage of another entity or individual (such an embodiment will be described further below in conjunction with FIG. 7A).

In the embodiment shown in FIG. 4, the mobile device is operated by an individual or entity seeking to verify the extent of their own coverage. Prior to processing of the steps of FIG. 4, a user operating a mobile device 500 is presumed to have installed and (if necessary) configured a mobile insurance application pursuant to the present invention. The mobile insurance application may be installed from the mobile device (e.g., by interacting with an application download system), or from a personal computer in communication with the mobile device. The application may be downloaded from the insurance company 320 or from an application marketplace (such as the iTunes® Store or Android® Store). Further, in some embodiments, prior to processing at 402, the user is presumed to have performed any configuration or personalization of the mobile insurance application. For example, the user may have entered information about themselves as well as their policy information so that the mobile insurance application may communicate with the insurance company and so that the user's policy information may be accessed from the mobile device 500. In some embodiments, the user may be prompted to enter verification information used to authenticate the user with the insurance systems.

As shown, processing of FIG. 4 begins at 402 where a user operating a mobile device 500 requests information regarding insurance coverage for an activity or event. As an example, a user who is a contractor or service provider may perform processing at 402 before beginning a new project or job to ensure that the policy covers the performance of the project or job. As another example, a user who is a driver may perform processing at 402 before operating a vehicle in a foreign country.

The request at 402 is transmitted to the insurance company (such as company 320 of FIG. 3) for processing. In some embodiments, the mobile insurance application appends any identifying information associated with the user and the user's insurance policy to the request so that the insurance company may quickly process the request.

Processing continues at 404 where a determination is made whether the activity or event is covered by the existing insurance policy. The determination may be made by comparing the information about the activity or event (from 402) with existing policy terms and conditions. If processing at 404 indicates that the event or activity is a covered event or activity, processing continues at 406 where a certificate or confirmation of coverage is returned. In some embodiments, the certificate or conformation of coverage may also be provided to one or more third parties (e.g., to provide proof of insurance coverage).

If processing at 404 indicates that the event or activity is not a covered event or activity, processing may continue at 408 where the user of the mobile device 500 is prompted or instructed to provide further details and information about the proposed activity so that additional coverage may be obtained. For example, the user may be prompted to provide details of where, how, and when the activity or event may occur as well as a detailed description of the activity or event. In some embodiments, the user may be prompted to obtain photos or images associated with the proposed activity or event (e.g., such as a photo of a job site, etc.). The data collected at 408 may be appended with additional data captured by the mobile insurance application to further enhance the application. For example, a time stamp, geolocation data, or the like may be obtained and appended to the data collected at 408.

The data is transmitted to the insurance company for processing. At 410, the insurance company may return detailed terms and conditions associated with obtaining coverage for the proposed activity or event. The user may review and either accept or decline the terms and conditions at 412. If the user declines the terms and conditions, processing continues at 414 where the insurance company transmits a message to the mobile device for display to the user indicating that the activity is not covered. If the user accepts the terms and conditions, processing continues at 416 where the insurance company binds the coverage. Processing continues at 406 where the user is presented with proof of insurance coverage (which may also be transmitted to other parties to prove or verify the coverage).

In this manner, embodiments allow users to easily obtain proof of insurance when and where they need it. Further, in the event that an activity or event is not covered by a current policy, embodiments allow users to easily request, and in some situations, bind new coverage so that suitable proof of insurance may be had.

Further details of some embodiments of mobile devices that may be used in conjunction with embodiments of the present invention will now be described by reference to FIGS. 5 and 6. Reference is first made to FIG. 5, where details of a mobile device 500 according to some embodiments is shown. As depicted, the mobile device 500 includes a number of components which may be controlled or perform functions in conjunction with one more application programs 510-512 to perform the features of some embodiments.

The mobile device 500 can include a memory interface 502 one or more data processors, image processors and/or central processing units 504, and a peripherals interface 506. The memory interface 502, the one or more processors 504 and/or the peripherals interface 506 can be separate components or can be integrated in one or more integrated circuits. The various components in the mobile device 500 can be coupled by one or more communication buses or signal lines.

Sensors, devices and subsystems can be coupled to the peripherals interface 506 to facilitate multiple functionalities. For example, one or more sensors, including biometrics sensors 514 and 528, an accelerometer 516, a photoelectric device 516, a proximity sensor 520, a camera 522, a wireless communication unit 524, and an audio unit 526 may be provided to facilitate the collection, use and interaction with data and information and to achieve the functions of the insurance applications described herein.

The mobile device 500 may include one or more input/output (I/O) devices and/or sensor devices. For example, input controllers 534 may be provided with a speaker and a microphone (not shown) to facilitate voice-enabled functionalities, such as phone and voice mail functions. In some implementations, a loud speaker can be included to facilitate hands-free voice functionalities, such as speaker phone functions. An audio jack can also be included for use of headphones and/or a microphone.

The I/O subsystem 530 can include a touch screen controller 532 and/or other input controller(s) 534. The touch-screen controller 532 can be coupled to a touch screen 536. The touch screen 536 and touch screen controller 532 can, for example, detect contact and movement or break thereof using any of a plurality of touch sensitivity technologies, including but not limited to capacitive, resistive, infrared, and surface acoustic wave technologies, as well as other proximity sensor arrays or other elements for determining one or more points of contact with the touch screen 536.

The other input controller(s) 534 can be coupled to other input/control devices 538, such as one or more buttons, rocker switches, thumb-wheel, infrared port, USB port, and/or a pointer device such as a stylus. The one or more buttons (not shown) can include an up/down button for volume control of the speaker and/or the microphone. In some implementations, a proximity sensor 520 can be included to facilitate the detection of the user positioning the mobile device 500 proximate to the user's ear and, in response, to disengage the touch-screen display 536 to prevent accidental function invocations. In some implementations, the touch-screen display 536 can be turned off to conserve additional power when the mobile device 500 is proximate to the user's ear.

Other sensors can also be used. For example, in some implementations, a photoelectric device 518 may be provided to facilitate adjusting the brightness of the touch-screen display 538. In some implementations, an accelerometer 516 can be utilized to detect movement of the mobile device 500. In some embodiments, the mobile device 500 may include circuitry and sensors for supporting a location determining capability, such as that provided by the global positioning system (GPS) or other positioning system (e.g., systems using Wi-Fi access points, television signals, cellular grids, Uniform Resource Locators (URLs)). In some implementations, a positioning system (e.g., a GPS receiver) can be integrated into the mobile device 500 or provided as a separate device that can be coupled to the mobile device 500 through a peripherals interface 506 to provide access to location-based services. Data from the location or positioning system(s) may be transmitted to an insurance company for analysis and for determining whether an insured's usage patterns, activity or location indicate that additional coverage may be required. For example, the location data may be used to determine whether a contractor is working on a new (and uncovered) job site, whether a driver is outside of (or will likely become outside of) a geographical coverage area, or the like. The location data may further be used, in some embodiments, to trigger warnings or alerts relating to natural disasters or impending events that may affect the insured (such as forest fires, hurricanes or the like). Further details of some embodiments which use such location data to trigger notices regarding such events are provided further below in conjunction with FIGS. 8 and 9.

The positioning and location-based services may be used, for example, to tag data transmitted from the mobile device 500 to insurance provider systems 102. For example, such location data may be appended to requests for insurance coverage (e.g., such as the data submitted at 408 in FIG. 4, above). In this way, location based data may be used to enhance application processing, reducing fraudulent applications and improving the insurer's ability to quickly and accurately process requests for insurance.

The mobile device 500 can also include a camera lens and sensor 520. In some implementations, the camera lens and sensor 520 can be located on the back surface of the mobile device 500. The camera can capture still images and/or video. The camera may be used, for example, to capture images of items, areas or information relevant to requests for insurance coverage. In some embodiments, the camera may be used as a scanner to obtain a bar code image or other code to verify an individual or entity's insurance coverage (e.g., as discussed below in conjunction with FIG. 7A). The camera may further be used to capture images to be used to prove the status of an item or activity, including as proof of compliance with terms of a policy or steps taken to remediate or prevent a loss.

The mobile device 500 can also include one or more wireless communication subsystems 524, such as an 802.11b/g communication device, and/or a Bluetooth® communication device. Other communication protocols can also be supported, including other 802.x communication protocols (e.g., WiMax, Wi-Fi), code division multiple access (CDMA), global system for mobile communications (GSM), Enhanced Data GSM Environment (EDGE), 3G (e.g., EV-DO, UMTS, HSDPA), etc.

In some implementations, additional sensors or subsystems may be coupled to the peripherals interface 506 via connectors such as, for example a Universal Serial Bus (USB) port, or a docking port, or some other wired port connection.

The memory interface 502 can be coupled to memory 508. The memory 508 can include high-speed random access memory and/or non-volatile memory, such as one or more magnetic disk storage devices, one or more optical storage devices, and/or flash memory (e.g., NAND, NOR). The memory 508 can store an operating system, such as Darwin, RTXC, LINUX, UNIX, OS X, WINDOWS, or an embedded operating system such as VxWorks. The operating system may include instructions for handling basic system services and for performing hardware dependent tasks. In some implementations, the operating system can be a kernel (e.g., UNIX kernel).

The memory 508 may also store application programs 510-512 which act, in conjunction with the processors 504, to cause the mobile device to operate to perform certain functions, including the insurance processing and insurance verification related functions described herein. In some embodiments, a payment application program may be provided to store payment account information and to provide a user access to funds deposited or paid by an insurance company. The payment application program may allow a user to access an account funded by an insurance company and, in some embodiments, may allow the mobile device 500 to function as a payment device. For example, in an embodiment where an insurance company uses features of the present invention to provide their insureds with access to funds associated with claims made (or advances associated with possible claims), the payment application program may display a payment account number, verification data, and a current balance of the account, so the payment account can be used in purchase transactions. The payment application program may also be operated to generate a representation of a payment card image with the payment account number and verification data displayed on a display device of the mobile device 500, allowing the payment account to be accessed at point of sale terminals. In some embodiments, an RFID chip or device may further be installed in the mobile device 500, allowing the payment device to be used in contactless payment transactions (e.g., such as those compliant with the PayPass® standard promoted by MasterCard International Incorporated). The payment application may provide other mechanisms allowing the user to retrieve, use and otherwise access the funds.

The memory 508 can also store data, including but not limited to documents, images, video files, audio files, and other data. In some implementations, the memory 508 stores address book data, which can include contact information (e.g., address, phone number, etc.) for one or more persons, organizations, services, or entities. For example, in some embodiments, the memory stores insurance policy numbers or other unique identifiers to allow a user of the mobile device 500 to quickly access insurance policy related data and information. In some embodiments, product or item data collected under control of the mobile insurance application may be stored in the memory 508 (either temporarily or for longer periods).

Figure 6:
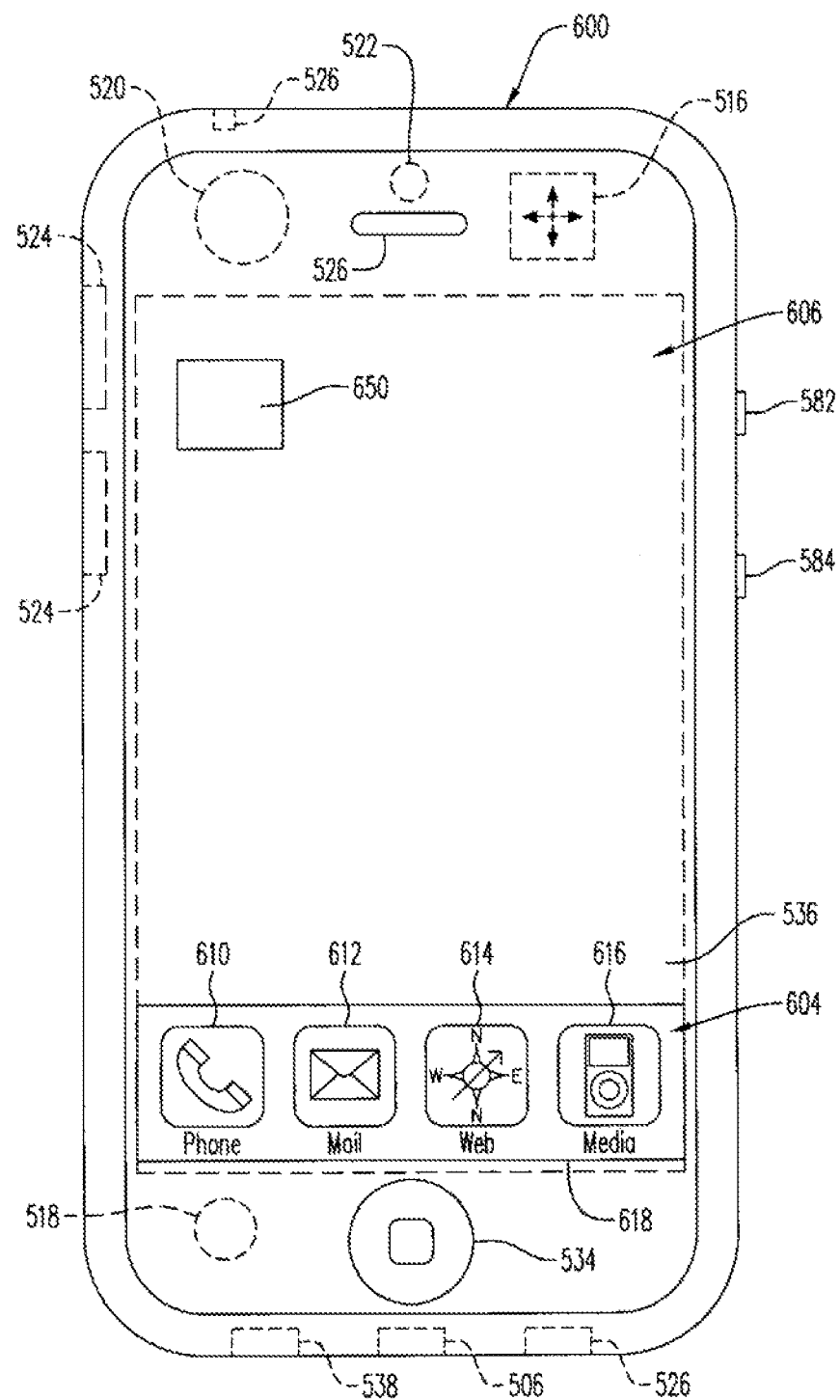
FIG. 6 is a block diagram of the mobile device of FIG. 5.

Reference is now made to FIG. 6, where a mobile device 500 is shown. As shown, the mobile device 500 can launch (and operate under the control of) one or more application programs by selecting an icon associated with an application program. As depicted, the mobile device 500 has several application programs (and corresponding icons), including an mobile insurance application (launched by selecting icon 650), a phone application (launched by selecting icon 610), an email program (launched by selecting icon 612), a Web browser application (launched by selecting icon 614), and a media player application (launched by selecting icon 604). Those skilled in the art will recognize that mobile device 500 may have a number of different icons and applications, and that applications may be launched in other manners as well (e.g., using hot keys, drop down selectors, or the like). In the embodiment shown, an application, such as the mobile insurance application, is launched by the user tapping or touching an icon displayed on the touch screen 536 interface of the mobile device 500.

Once an application is launched, the user may interact with the application, and the mobile device may function pursuant to the program instructions associated with the application. For example, once the mobile insurance application is launched, a user may perform the process of FIG. 4, described above, or FIG. 8, described below. In the mobile insurance applications described herein, details of some aspects of the operation of the mobile device 500 are described; however, those skilled in the art will appreciate that a number of different functions and operational features may be provided.

Figure 7A:
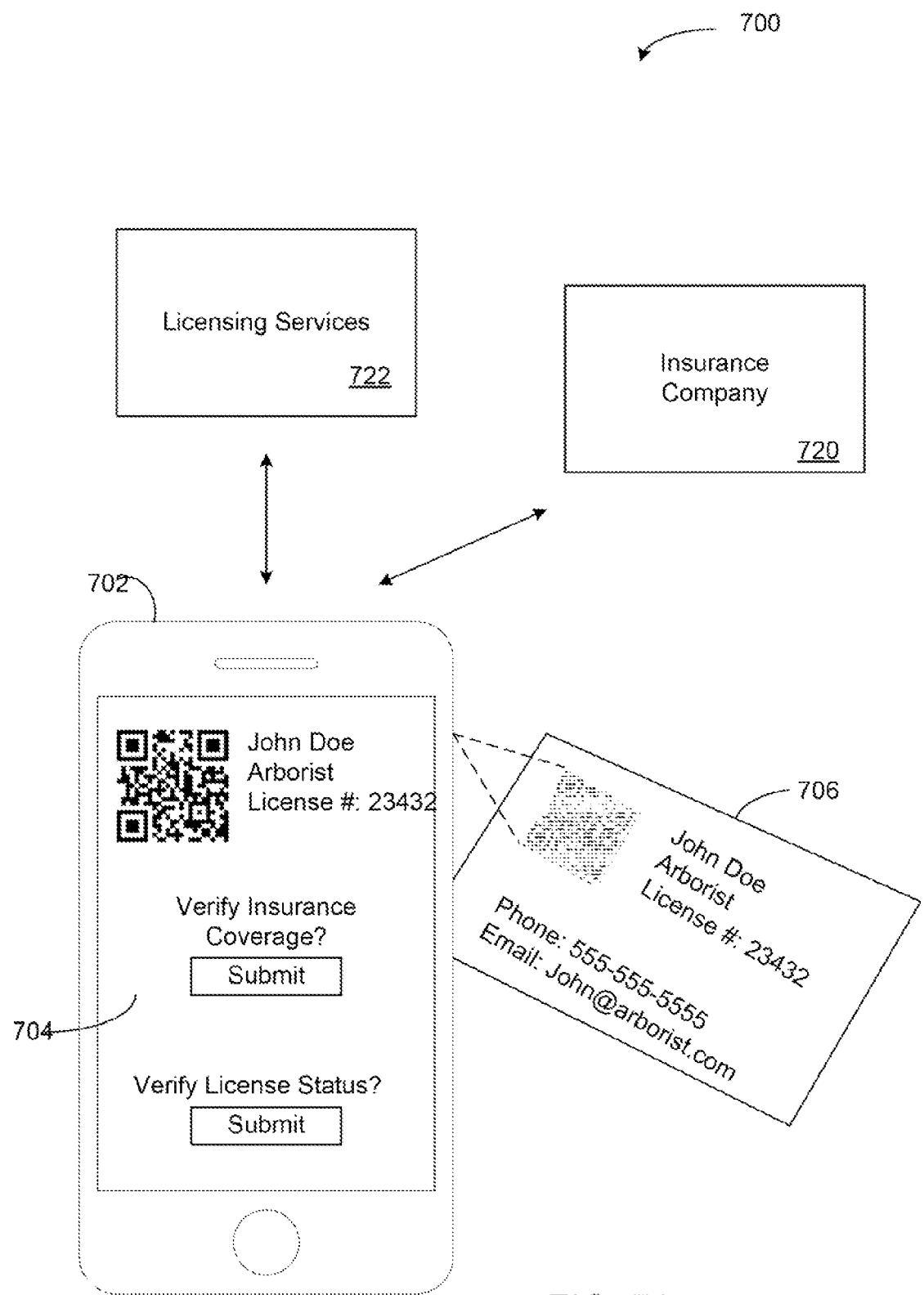
FIG. 7A-7C are block diagrams illustrating user interfaces pursuant to some embodiments.
Figure 7B:
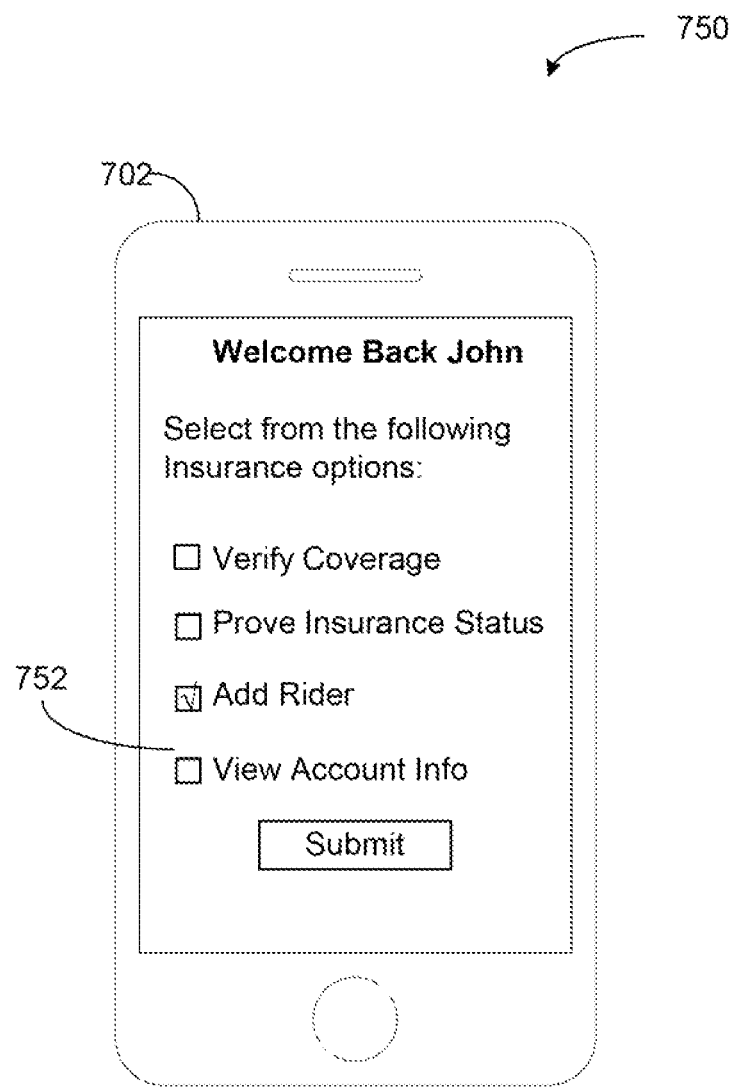
Figure 7C:
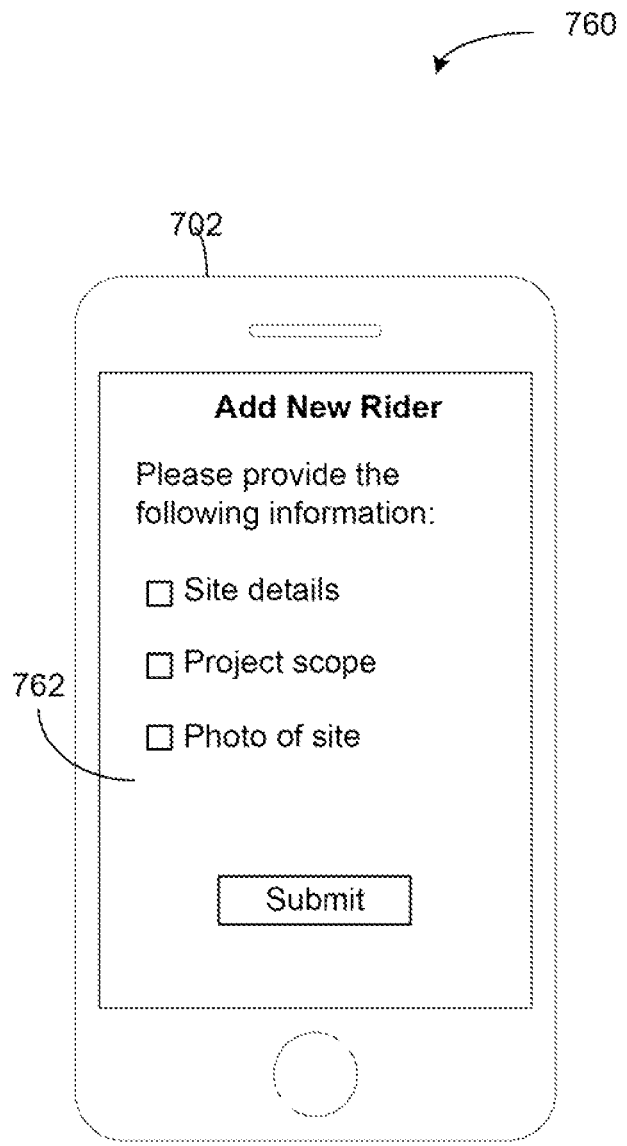

Reference is now made to FIGS. 7A-C, which show block diagrams 700-760 of a mobile device 708 operating a mobile insurance application pursuant to the present invention. For example, referring first to FIG. 7A, a block diagram 700 is shown in which a user is operating a mobile device 702 which is configured to execute a mobile insurance application of the present invention to verify information associated with a service provider. The mobile device 702 is in communication with remote systems including a licensing services provider 722 and an insurance company 720 and is operated to allow a user to verify the insurance status and the licensing status of a service provider by scanning information on the service provider's business card 706. The card 706 has the service provider's contact information printed on it as well as a two dimensional bar code (shown as a QC Code, although those skilled in the art will appreciate that other coding techniques may be used). The bar code has information encoded on it that may be read by mobile devices operating mobile insurance applications pursuant to the present invention. For example, the bar code may encode an identifier that may be transmitted from the mobile device 702 to remote systems including a licensing services provider 722 and insurance company 720. The remote systems may use the identifier to retrieve information about the licensing and insurance coverage status of the service provider.

The mobile insurance application may cause a display screen 704 to be presented to a user of the mobile device 702 prompting the user to select one of several options to verify information about the service provider (e.g., the user may select to verify a licensing status and/or an insurance coverage status). In this manner, users of mobile devices may easily and confidently identify whether individuals or entities are licensed and have sufficient insurance coverage to perform an activity or undertake an event.

Reference is now made to FIG. 7B where a further block diagram 750 is shown in which the mobile device 702, operating a mobile insurance application of the present invention, is operated to perform further insurance verification processes. In the embodiment shown, the mobile device is operated by an insured individual ("John"), and presents the user with several options related to the verification of insurance coverage. The user may select one or more options which cause the mobile device to interact with a remote insurance provider (not shown) to perform various insurance verification activities, including, for example, the option to verify coverage, to prove insurance status (e.g., to a third party), to add additional coverage or a rider, and to view account information.

Reference is now made to FIG. 7C where a further block diagram 760 is shown in which the mobile device 702, operating a mobile insurance application of the present invention, is operated to perform actions related to obtaining additional insurance coverage for a specific activity or event. The user, as shown, is prompted to enter additional information that will be used by the insurance company to analyze and, if appropriate, bind the additional coverage. For example, the additional information may include further information about a job site or activity for which additional insurance coverage is desired, details about the proposed project scope, and one or more photos or other details associated with the job site.

Pursuant to some embodiments, insured individuals or entities may be reminded or prompted to consider obtaining additional insurance coverage based on information collected by their mobile device. For example, a driver who is about to leave a geographical coverage area may be prompted to consider obtaining additional coverage for the new geographical area. A contractor who is performing work on a new job site may be prompted to obtain coverage for the new site. A carpenter who is working on a type of project that is not covered by his current policy may be prompted to obtain coverage for the new type of project. An employee covered by a workers compensation policy who is performing work in an area not covered by the policy may result in a notification being sent to the employer (or an adjustment to the workers compensation policy). Each of these scenarios, and others, are examples of types of situations in which embodiments of the present invention may be used. A process 800 for reminding or prompting insured individuals or entities to consider obtaining additional insurance coverage based on information collected by mobile devices will now be described by reference to FIG. 8.

The process 800 may be performed by an insurance company (e.g., such as the insurance company 320 of FIG. 3) or an agent of an insurance company by processing data received from one or more mobile devices configured to operate pursuant to the present invention. The process 800 relates to embodiments where insured individuals or entities agree to participate in a monitoring or notification program in which data from their mobile device(s) are transmitted to the insurance company for evaluation in order to identify whether additional insurance coverage may be required for an activity or whether circumstances warrant a notification, warning or other alert relating to an insurance policy. In some embodiments, participants in such a monitoring program may receive discounts or other benefits in exchange for sharing the data.

Figure 8:
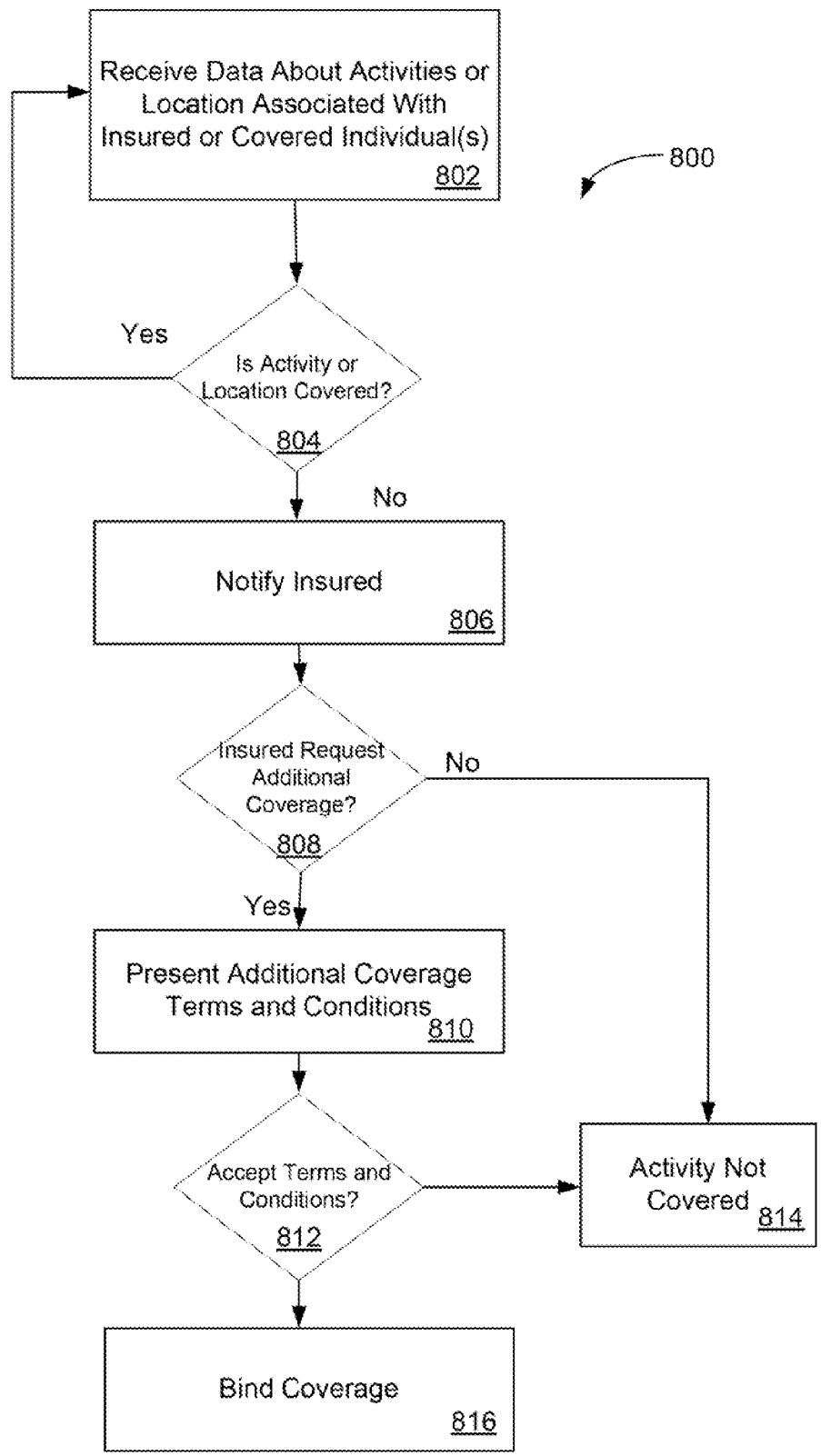
FIG. 8 is a flow diagram depicting a proof of insurance process pursuant to some embodiments.

Prior to processing of the steps of FIG. 8, a user operating a mobile device is presumed to have installed and configured a mobile insurance application. For example, the user may have consented to share data from the mobile device with the insurance company, and may have provided information that will allow the insurance company to evaluate the data to identify activities or events that may require additional insurance coverage. Examples of several illustrative, but not limiting, configurations are provided further below in conjunction with FIG. 9.

The process 800 begins at 802 where the insurance company 320 receives data about activities or location associated with insured or covered individual(s). The data is received from one or more mobile devices operating a mobile insurance application pursuant to the present invention. The data may include a number of different types of data, including location data or other data collected by sensor(s) of the mobile device. In some embodiments, the data may be aggregated and partially analyzed by the mobile application before it is transmitted to the insurance company. For example, in a situation where the user of the mobile device is a driver with an insurance policy that has a geographical coverage area, the mobile application may collect location data from location sensors in the mobile device. The location data may be aggregated in the mobile application and only transmitted to the insurance company 320 when the data indicates that the mobile device is going to (or has) passed outside the geographical coverage area. In this way, less data need be transmitted from the mobile device to the insurance company 320.

As another example, in a situation where the insured is a property owner (including homeowners, vehicle owners, business owners, or the like), the insured may consent to provide location information in order to receive alerts or warnings related to severe weather or other conditions that may affect the insured's property. Those skilled in the art, upon reading this disclosure, will appreciate that other types of locations or activity data may also be collected and used to identify activities or locations that require additional insurance coverage or information about coverage, and that the disclosed embodiments are not exhaustive.

Processing continues at 804 where the insurance company 320 determines whether the activity or location of the mobile device 330 is covered. This determination may be made by comparing the data received at 802 with stored data associated with the insurance policy(s) and coverage information related to the user. For example, continuing the illustrative example where the user is an insured driver, processing at 804 may include comparing location data received at 802 with terms of the driver's insurance policy to determine that the driver is outside the geographical area of coverage.

If processing at 804 indicates that the activity or location is covered, processing continues at 802 when further information is received from the mobile device 330. The further information may be received at a later time, such as on a scheduled basis or when additional data is available from the mobile device 330.

Figure 9A:
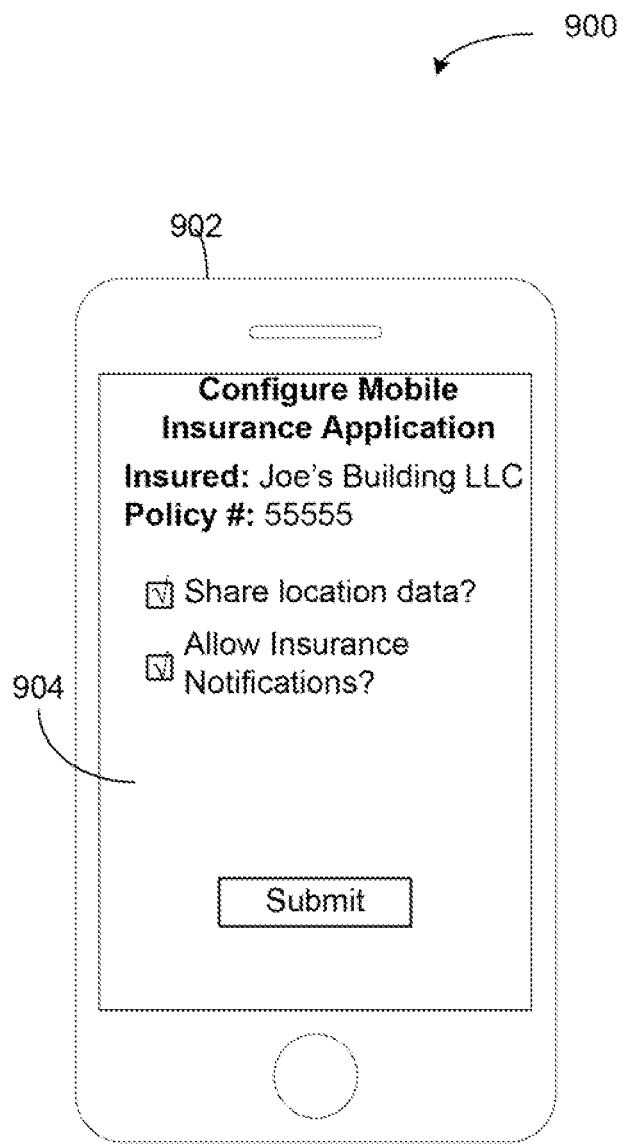
FIG. 9A-9D are block diagrams illustrating user interfaces pursuant to some embodiments.
Figure 9B:
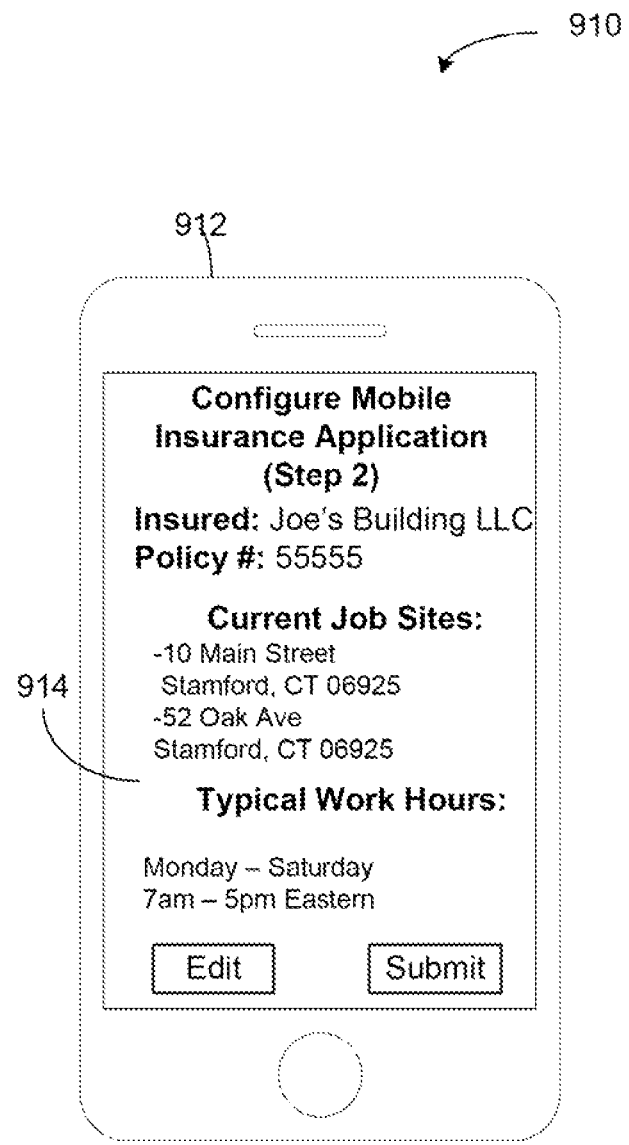
Figure 9C:
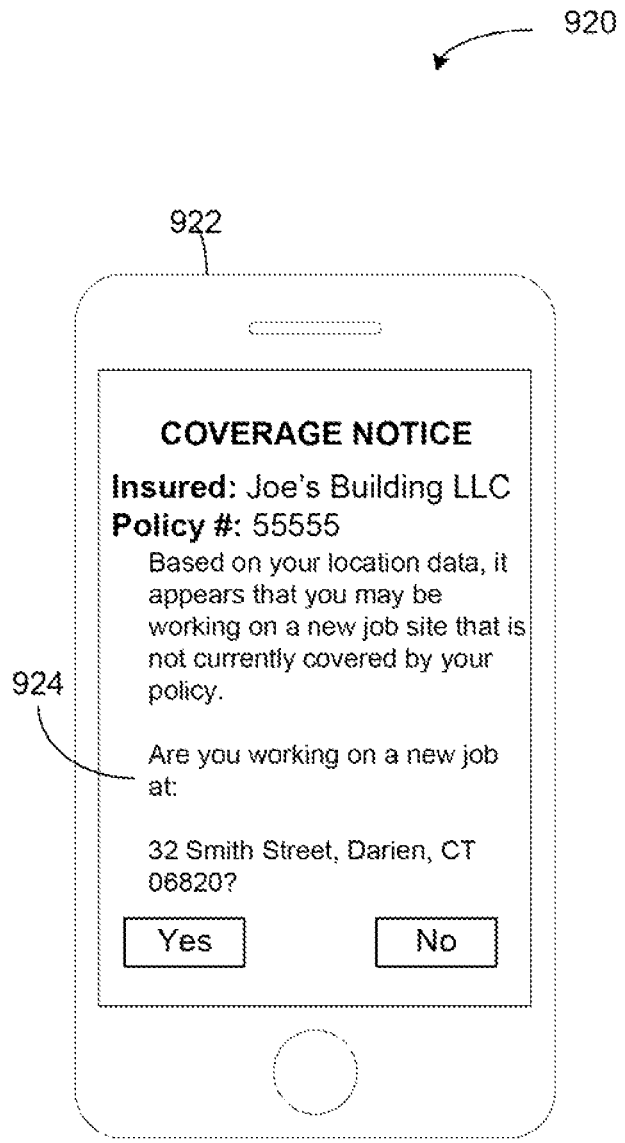
Figure 9D:
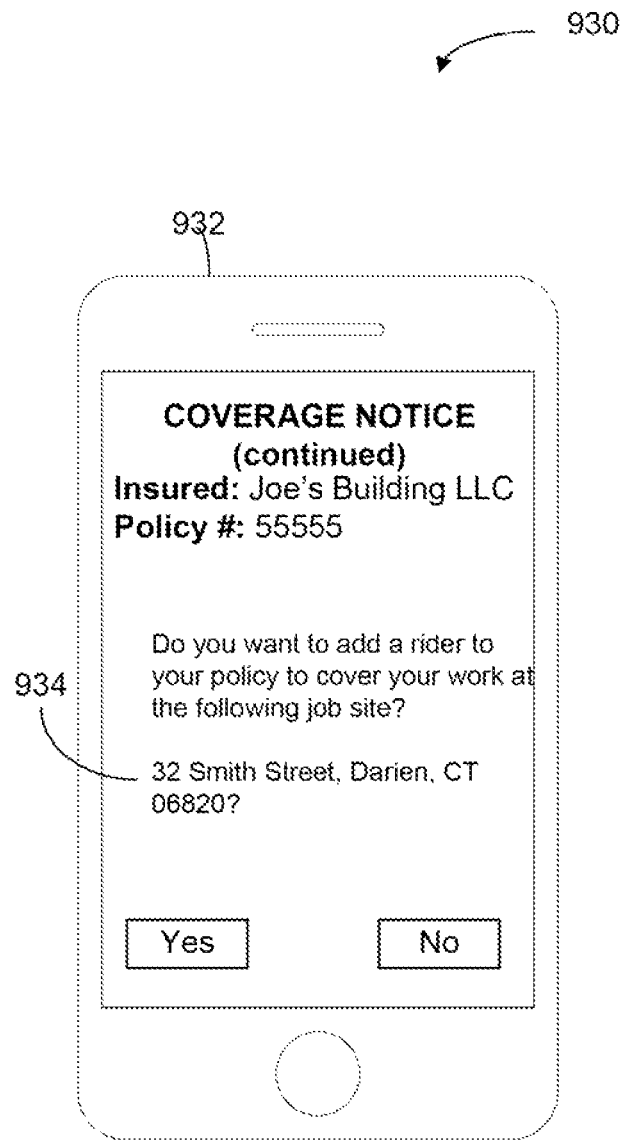

If processing at 804 indicates that the activity or location is not covered, processing continues at 806 where the insured is notified of the lack of coverage. The notification may be provided in a number of different ways, including by transmitting a message to the mobile device for display to the user. For example, an SMS message may be transmitted providing information about the lack of coverage, or an alert may be transmitted to the mobile insurance application causing a message to be displayed on a display screen of the mobile device 330 (e.g., such as the alert shown in FIG. 9C, below). The notification provided at 806 may include information allowing the insured to request additional coverage to ensure that the uncovered activity or location be sufficiently covered. For example, as shown in FIG. 9D, the insured may be prompted to select whether they want additional coverage or not.

In some embodiments, the alert or notification may include information such as emergency information, evacuation instructions (in the case of a natural disaster or severe weather), information about preparing for and remediating damage associated with an impending event, or the like.

Processing continues at 808 where a determination is made whether the insured requests additional coverage or not. If the insured declines the additional coverage, processing continues at 814 and the activity or location is not covered. A notification may be provided to the insured informing them of the risk of not accepting the additional coverage.

If processing at 808 indicates that the insured wants the additional coverage, processing continues at 810 where the terms and conditions of the additional coverage are presented to the insured. The terms and conditions may be generated by the insurance company based on further information received from the insured about the nature of the activity or location. For example, continuing the illustrative example of a driver who is outside their geographical area of coverage, the insurance company 320 may request details about the scope and nature of the insured's travel outside the geographical area of coverage.

Processing continues at 812 where a determination is made whether the insured accepted the terms and conditions of the additional coverage. If the insured declines the terms and conditions, processing continues at 814 and the activity or location is not covered. A notification may be provided to the insured informing them of the risk of not accepting the additional coverage.

If the insured accepts the terms and conditions, processing continues at 816 and the additional coverage is bound. In this manner, insured individuals or entities can be assured that their activities or locations are appropriately covered by their insurance. The insurance company 320 (or an agent or third party) processes data received from a mobile device operated by the insured to identify activities or locations which are not covered and to inform the insured of the lack of coverage. Further, the insured may obtain additional coverage quickly and efficiently using the mobile insurance application of the present invention.

In some embodiments, a further processing step (not shown) may be performed in the event that an insured is eligible for a payment under a policy. For example, in situations where the activity for which additional insurance coverage was obtained and for which the insurance company has sufficient information to assess that a claim or payout is required, embodiments allow for the delivery of the payment (or a portion of the payment) to the mobile device 330 for access by the insured (e.g., using a payment application associated with the mobile device 330). As a specific illustrative (but not limiting) example where an insured is a homeowner having homeowners insurance covering fire damage, in the event of a forest fire impacting an area near the homeowner's property, the homeowner may be temporarily displaced from her home. The insurance policy may provide coverage for such short term displacement, providing funds for temporary lodging and food. Pursuant to some embodiments, in such a situation, the homeowner may be notified (e.g., at 806) of the fire, and may further be provided with funds accessible via the mobile device 330.

Reference is now made to FIGS. 9A-9D which represent a series of user interfaces that may be presented to a user of a mobile device based on the processing associated with the process 800 of FIG. 8. The user interfaces relate to an illustrative example where the insured is a contractor ("Joe's Building LLC"). The insured has a small commercial lines insurance policy (policy number "55555") and has installed a mobile insurance application on his mobile device. In a first user interface 904 (shown in FIG. 9A), the insured is presented with a screen prompting for configuration data. In particular, the insured is asked to opt in to share location data as well as to allow insurance notifications to be received. Other configuration information may also be provided, these options are shown for the purpose of illustration only. In the illustrative user interface, the insured opts in to both share location data and to allow insurance notifications to be received. In a second illustrative user interface 914 (shown in FIG. 9B), the insured provides additional details that will be used by the insurance company to monitor data received to identify whether activities or locations are covered. In the illustrative user interface 914, the insured is asked to confirm the current construction or job sites that the construction firm is working on, as well as the firm's typical work hours. Other information may also be requested to allow the insurance company to more accurately identify activities or locations that are outside the current scope of coverage.

Once the insured has provided the configuration information, the mobile insurance application may operate in the background when the user operates their mobile device. For example, the mobile insurance application may collect data associated with the location of the mobile device and transmit some location data to the insurance company. The insurance company analyzes the data and determines if the data suggest that the insured may need additional coverage for an activity or location. In the illustrative example of "Joe's Building LLC", the mobile insurance application may collect data to identify whether the insured is spending time during his working hours at a new location, from which the insurance company may infer that the insured is working at a new job site that is not currently covered by the commercial lines insurance policy. A coverage notice may then be presented to the insured on a display screen of his mobile device (as shown in FIG. 9C) informing the insured that, if the new location is a new job site, it is not currently covered. The insured may be prompted to confirm that the new location is a new job site. If so, a user interface 934 (shown in FIG. 9D) may be presented to the insured prompting whether the insured wishes to add a rider to cover the new job site.

Those skilled in the art will appreciate that similar user interfaces and interactions may be provided for other types of insurance coverage, and that features of the present invention may be used to monitor activities and locations to identify situations where additional insurance coverage may be required. Further, although embodiments have been described in which data is collected from a single mobile device, some embodiments may involve the collection of data from multiple devices. As an example, a contractor who has a number of employees who operate mobile devices may install a mobile insurance application on each of the mobile devices so that data from each mobile device may be collected and used to identify possible coverage issues as well as to provide proof of insurance as needed.

The data collected using such techniques may be used by insurance providers and other entities to make insurance related decisions where legally allowed.

Thus, embodiments of the present invention allow mobile device users to easily and quickly verify insurance status (of their own policies or the policies of others) as well as to obtain additional coverage where needed. Although the present invention has been described in connection with specific exemplary embodiments, it should be understood that various changes, substitutions, and alterations apparent to those skilled in the art can be made to the disclosed embodiments without departing from the spirit and scope of the invention as set forth in the appended claims.

What is claimed is:

1. A computer system, comprising:
   a server computer system, comprising:
      a data storage device for storing data defining a plurality of insurance policies and a plurality of insurance coverage rules associated with one or more of said insurance policies, at least one of said insurance policies associated with a mobile insurance application operated by an insured, wherein a location-based insurance coverage rule associated with the insured defines a geographical coverage area within which an activity by the insured is covered by said least one insurance policy and outside of which the activity by the insured is not covered by said at least one insurance policy;
      a computer processor for executing program instructions and for retrieving said data defining a plurality of insurance policies from the data storage device;
      a memory, coupled to the computer processor, for storing program instructions for execution by the computer processor to
         receive, from a mobile device associated with said mobile insurance application, location data collected from at least a first sensor of said mobile device, the at least first sensor automatically controlled to collect said location data by operation of said mobile insurance application based on configuration data associated with said at least one of said insurance policies;
         determine, based at least in part on said location data and the location-based insurance coverage rule, that the activity associated with said insured is not covered by said at least one insurance policy because the insured is not within the geographical coverage area;
         transmit, to said mobile device, information indicating that the activity is not covered by said at least one insurance policy; and
         provide funds, associated with a claim, to a payment account for the insured;
         wherein the insured is a worker and said at least one of said insurance policies is a commercial job site-based insurance policy, and said program instructions for execution by the computer processor to transmit information indicating that work performed by the worker is not covered by the commercial job site-based insurance policy because the worker's current location is not within the geographical coverage area; and
      a mobile device in communication with the server computer system, the mobile device comprising a memory and a processor, the memory storing an application program, the application program causing the mobile device processor to: present a user interface prompting for configuration data including at least one or more current work locations and work hours; after receiving the configuration data, execute the configured application program in the background to control the at least first sensor of the mobile device to collect data indicative of location of the mobile device away from the at least one or more current work locations during the received work hours, and to transmit selectively the collected location data to the server computer system, the mobile device further being configured to execute a payment application program to access the payment account, and the mobile device comprising an RFID unit configured to provide contactless payment from the payment account;
      wherein the processor is further configured to access the data indicative of whether the insured is spending time during working hours at the new location, the processor being further configured to generate a coverage notice for presentation to the insured via the application program on the mobile device.

2. The computer system of claim 1, further comprising program instructions for execution by the computer processor to:
   receive information from said mobile device identifying a scope of work to be performed at the worker's current location;

receive a request from said mobile device to add an additional job-site to the geographical coverage area based on the worker's current location; and generate terms and conditions for said additional commercial job site-based insurance policy coverage based on said information identifying the scope of the work.

3. The computer system of claim 1, wherein said location data is collected under control of said mobile insurance application and transmitted to said insurance system under control of said mobile insurance application.

4. The computer system of claim 1, wherein said location data is collected under control of said mobile insurance application on request by said insured.

5. A computer system for reconciling data received from mobile devices with stored data indicative of location-based rules, comprising:

a server computer system, comprising:
  a data storage device for storing data defining a plurality of insurance policies and a plurality of insurance coverage rules associated with one or more of said insurance policies, at least one of said insurance policies associated with a mobile insurance application operated by an insured, wherein a location-based insurance coverage rule associated with the insured defines a geographical coverage area within which an activity by the insured is covered by said least one insurance policy and outside of which the activity by the insured is not covered by said at least one insurance policy;
  a computer processor for executing program instructions and for retrieving said data defining a plurality of insurance policies from the data storage device;
  a memory, coupled to the computer processor, for storing program instructions for execution by the computer processor to
    receive, from a mobile device, location data collected by the mobile device;
    determine, based at least in part on said location data and the location-based insurance coverage rule, that the activity associated with said insured is not covered by said at least one insurance policy because the insured is not within the geographical coverage area;
    transmit, to said mobile device, information indicating that the activity is not covered by said at least one insurance policy; and
    provide funds, associated with a claim, to a payment account for the insured;
  wherein the insured is a driver and said at least one of said insurance policies is an automobile insurance policy associated with an automobile being operated by the driver, and said program instructions for execution by the computer processor to transmit information indicating that operation of the automobile by the driver is not covered by the automobile insurance policy because the driver's current location is not within the geographical coverage area;
  further comprising program instructions for execution by the computer processor to:
    receive a request from said mobile device to expand the geographical coverage area of the automobile insurance policy to include the driver's current location; and
    transmit, to said mobile device, terms and conditions for said additional automobile insurance policy coverage; and a mobile device executing instructions of a mobile insurance application program, the program configured, based on configuration data associated with said at least one of said insurance policies, to control the mobile device to collect location data from at least a first sensor of the mobile device, and to aggregate location data collected from the at least first sensor and to transmit the aggregated location data only when the data indicates that the mobile device is going to or has passed outside of the geographical coverage area;

the mobile device further being configured to execute a payment application program to access the payment account, and the mobile device comprising an RFID unit configured to provide contactless payment from the payment account.

6. A computer-implemented method, comprising:

presenting, by a processor of a mobile device, associated with an insured entity, executing instructions of an application program stored in a memory of the mobile device, a user interface prompting for configuration data including at least one or more current work locations and work hours;

after receiving the configuration data, executing, by the processor of the mobile device, the configured application program in the background to control at least a first sensor of the mobile device to collect data indicative of location of the mobile device away from the at least one or more current work locations during the received work hours, transmitting, by the mobile device, selectively, the collected location data to a server computer system;

receiving, by the server computer system, from the mobile device, the collected and selectively transmitted location data;

accessing, by an insurance processing computer, the data indicative of whether the insured is spending time during working hours away from the at least one or more current work locations; determining, by the insurance processing computer, that an activity associated with said insured entity is not covered by a plurality of insurance coverage rules, the determining based at least in part on said received location data and a comparison of said location data and data defining a plurality of insurance policies and a plurality of insurance coverage rules associated with one or more of said insurance policies, wherein the determining is further based at least in part on a location-based insurance coverage rule associated with the insured entity that defines a geographical coverage area within which the activity by the insured entity is covered by a first insurance policy and outside of which the activity by the insured entity is not covered by the first insurance policy;

transmitting, from the insurance processing computer to said mobile device, information indicating that the activity is not covered by the first insurance policy because of the location-based insurance coverage rule;

providing funds, associated with a claim, by the insurance processing computer, to a payment account for the insured;

presenting, by the processor of the mobile device executing instructions of the application, on a display screen of the mobile device, a notice that the activity is not covered by the first insurance policy because of the location-based insurance coverage rule; and executing, by the mobile device, a payment application program to access the payment account, and providing contactless payment from the payment account by an RFID unit of the mobile device;

wherein the insured entity is a worker and said insurance policy is a commercial job site-based insurance policy, and said transmitting information includes transmitting information indicating that work performed by the worker is not covered by the commercial job site-based insurance policy because the worker's current location is not within the geographical coverage area.

7. The method of claim 6, further comprising:

receiving information from said mobile device identifying a scope of work to be performed at the worker's current location;

receiving a request from said mobile device to add an additional job site to the geographical coverage area based on the worker's current location; and generating terms and conditions for said additional commercial job site-based insurance policy coverage based on said information identifying the scope of the work.

8. The method of claim 6, wherein said location data is collected under control of said mobile insurance application and transmitted to said insurance system under control of said mobile insurance application.

9. The method of claim 6, wherein said location data is collected under control of said mobile insurance application on request by said insured entity.

10. A computerized method, comprising:

collecting, by a mobile device, operated by an insured entity, executing instructions of a mobile insurance application program, the program configured based on configuration data associated with said at least one of said insurance policies, location data from at least a first sensor of the mobile device;

aggregating, by the mobile device, location data collected from the at least first sensor;

transmitting, by the mobile device, the aggregated location data only when the data indicates that the mobile device is going to or has passed outside of the geographical coverage area;

receiving, from the mobile device, the transmitted location data;

determining, by an insurance processing computer, that an activity associated with said insured entity is not covered by a plurality of insurance coverage rules, the determining based at least in part on said location data and a comparison of said location data and data defining a plurality of insurance policies and a plurality of insurance coverage rules associated with one or more of said insurance policies, wherein the determining is further based at least in part on a location-based insurance coverage rule associated with the insured entity that defines a geographical coverage area within which the activity by the insured entity is covered by a first insurance policy and outside of which the activity by the insured entity is not covered by the first insurance policy;

transmitting, from the insurance processing computer to said mobile device, information indicating that the activity is not covered by the first insurance policy because of the location-based insurance coverage rule;

providing funds, associated with a claim, by the insurance processing computer, to a payment account for the insured; and executing, by the mobile device, a payment application program to access the payment account, and providing contactless payment from the payment account by an RFID unit of the mobile device;

wherein the insured entity is a driver and said first insurance policy is an automobile insurance policy associated with an automobile being operated by the driver, and said transmitting includes transmitting information indicating that operation of the automobile by the driver is not covered by the automobile insurance policy because the driver's current location is not within the geographical coverage area; and further comprising the steps of:

receiving a request from said mobile device to expand the geographical coverage area of the automobile policy to include the driver's current location; and transmitting, to said mobile device, terms and conditions for said additional automobile insurance policy coverage.

11. A non-transitory, computer-readable medium storing program code executable by a computer to:

receive, from a mobile device associated with a mobile insurance application and operated by an insured entity, the application being configured by presenting a user interface prompting for configuration data including at least one or more current work locations and work hours, and the application further, after receiving the configuration data, executing in the background to control at least a first sensor of the mobile device to collect data indicative of location of the mobile device away from the at least one or more current work locations during the received work hours, and to transmit selectively the collected location data to the server computer system;

access, by an insurance processing computer, the data indicative of whether the insured is spending time during working hours away from the at least one or more current work locations; determine, by the insurance processing computer, that an activity associated with said insured entity is not covered by a plurality of insurance coverage rules, the determining based at least in part on said location data and a comparison of said location data and data defining a plurality of insurance policies and a plurality of insurance coverage rules associated with one or more of said insurance policies, wherein the determining is further based at least in part on a location-based insurance coverage rule associated with the insured entity that defines a geographical coverage area within which the activity by the entity is covered by a first insurance policy and outside of which the activity by the entity is not covered by the first insurance policy;

transmit, from the insurance processing computer to said mobile device, information indicating that the activity is not covered by the first insurance policy because of the location-based insurance coverage rule, the application program further causing the mobile device to present, on a display screen of the mobile device, a notice that the activity is not covered by the first insurance policy because of the location-based insurance coverage rule; and provide funds, associated with a claim, by the insurance processing computer, to a payment account for the insured, the mobile device further being configured to execute a payment application program to access the payment account, and the mobile device comprising an RFID unit configured to provide contactless payment from the payment account;

wherein the insured entity is a worker and said insurance policy is a commercial job site-based insurance policy, and said transmitting information includes transmitting information indicating that work performed by the worker is not covered by the commercial job site-based insurance policy because the worker's current location is not within the geographical coverage area.

12. The medium of claim 11, further storing program code executable by the computer to:
   receive information from said mobile device identifying a scope of work to be performed at the worker's current location;
   receive a request from said mobile device to add an additional job site to the geographical coverage area based on the worker's current location; and
   generate terms and conditions for said additional commercial job site-based insurance policy coverage based on said information identifying the scope of the work.

13. The medium of claim 11, wherein said location data is collected under control of said mobile insurance application and transmitted to said insurance system under control of said mobile insurance application.

14. The method of claim 11, wherein said location data is collected under control of said mobile insurance application on request by said insured entity.

15. A non-transitory, computer-readable medium storing program code executable by a computer to:
   receive, from a mobile device associated with a mobile insurance application and operated by an insured entity, location data collected from at least a first sensor of said mobile device said mobile insurance application automatically controlling said at least first sensor based on configuration data associated with at least a first insurance policy of said insured entity, wherein the mobile insurance application is further configured to aggregate location data collected from the at least first sensor and to transmit the aggregated location data only when the data indicates that the mobile device is going to or has passed outside of the geographical coverage area;
   determine, by an insurance processing computer, that an activity associated with said insured entity is not covered by a plurality of insurance coverage rules, the determining based at least in part on said location data and a comparison of said location data and data defining a plurality of insurance policies and a plurality of insurance coverage rules associated with one or more of said insurance policies, wherein the determining is further based at least in part on a location-based insurance coverage rule associated with the insured entity that defines a geographical coverage area within which the activity by the entity is covered by a first insurance policy and outside of which the activity by the entity is not covered by the first insurance policy;
   transmit, from the insurance processing computer to said mobile device, information indicating that the activity is not covered by the first insurance policy because of the location-based insurance coverage rule; and
   provide funds, associated with a claim, by the insurance processing computer, to a payment account for the insured, the mobile device further being configured to execute a payment application program to access the payment account, and the mobile device comprising an RFID unit configured to provide contactless payment from the payment account;
   wherein the insured entity is a driver and said first insurance policy is an automobile insurance policy associated with an automobile being operated by the driver, and said transmitting includes transmitting information indicating that operation of the automobile by the driver is not covered by the automobile insurance policy because the driver's current location is not within the geographical coverage area; and further storing program code executable by the computer to:
   receive a request from said mobile device to expand the geographical coverage area of the automobile policy to include the driver's current location; and
   transmit, to said mobile device, terms and conditions for said additional automobile insurance policy coverage.

* * * * *